(12) United States Patent
Niedzwiecki et al.

(10) Patent No.: US 11,452,710 B1
(45) Date of Patent: Sep. 27, 2022

(54) MICRONUTRIENT AND PLANT EXTRACT COMPOSITION AND METHOD OF IMPROVING BONE HEALTH

(71) Applicant: Matthias W Rath, Henderson, NV (US)

(72) Inventors: Aleksandra Niedzwiecki, Henderson, NV (US); Matthias W Rath, Henderson, NV (US); Lei Shi, Ann Arbor, MI (US); Anna Goc, Sanjose, CA (US)

(73) Assignee: Matthias W. Rath, Henderson, NV (US)

( * ) Notice: Subject to any disclaimer, the term of this patent is extended or adjusted under 35 U.S.C. 154(b) by 0 days.

(21) Appl. No.: 17/674,146

(22) Filed: Feb. 17, 2022

(51) Int. Cl.
| | | |
|---|---|---|
| *A61K 31/375* | (2006.01) | |
| *A61K 31/07* | (2006.01) | |
| *A61K 31/355* | (2006.01) | |
| *A61K 31/593* | (2006.01) | |
| *A61K 31/122* | (2006.01) | |
| *A61K 36/185* | (2006.01) | |
| *A61K 33/06* | (2006.01) | |
| *A61K 33/22* | (2006.01) | |
| *A61K 33/30* | (2006.01) | |
| *A61K 33/00* | (2006.01) | |
| *A61K 33/34* | (2006.01) | |
| *A61K 31/519* | (2006.01) | |

(52) U.S. Cl.
CPC ............ *A61K 31/375* (2013.01); *A61K 31/07* (2013.01); *A61K 31/122* (2013.01); *A61K 31/355* (2013.01); *A61K 31/519* (2013.01); *A61K 31/593* (2013.01); *A61K 33/00* (2013.01); *A61K 33/06* (2013.01); *A61K 33/22* (2013.01); *A61K 33/30* (2013.01); *A61K 33/34* (2013.01); *A61K 36/185* (2013.01)

(58) Field of Classification Search
CPC ........ A61K 33/22; A61K 33/30; A61K 33/06; A61K 33/00; A61K 31/375; A61K 31/07; A61K 31/593; A61K 31/355
See application file for complete search history.

(56) References Cited

U.S. PATENT DOCUMENTS

| 2007/0243210 A1* | 10/2007 | Keefe | .................. A23L 33/10 514/474 |
| 2020/0000864 A1* | 1/2020 | Shabani | .................. A61K 9/08 |

FOREIGN PATENT DOCUMENTS

| GB | 2585619 A * | 1/2021 | ........... A23L 33/155 |

OTHER PUBLICATIONS

Griffin (WebMD, Food Sources for Vitamins and Minerals, Jul. 26, 2020, https://www.webmd.com/food-recipes/guide/vitamins-and-minerals-good-food-sources) (Year: 2020).*
Medical News Today (Health Benefits and Possible Side Effects of MSM, 2021, https://www.medicalnewstoday.com/articles/324544) (Year: 2021).*
Poulson (Verywell health, Healthy foods that are high in boron, 2022, https://www.verywellhealth.com/best-boron-rich-foods-5092054) (Year: 2022).*
Peretz et al (Journal of Trace Elements in Medicine and Biology, 2001, vol. 15, pp. 175-178) (Year: 2001).*
Cidem et al (Rheumatology international, 2015, vol. 35, pp. 1739-1742) (Year: 2015).*
Guler et al (International Journal of Biological Macromolecules, online Sep. 2021, vol. 190, pp. 244-258) (Year: 2021).*

* cited by examiner

*Primary Examiner* — Mark V Stevens
(74) *Attorney, Agent, or Firm* — Geeta Kadambi; Riddhiip LLC (57) ABSTRACT

The micronutrient and plant extract composition comprises of a vitamin C, vitamin A (β-carotene), vitamin E, vitamin D3, vitamin K2, folic acid, calcium, magnesium, boron, horsetail extract, zinc, potassium, copper, methylsulfonyl-methane (MSM) and stinging nettle extract and in combination it is used for treating, and reversing bone demineralization. The micronutrient and plant extract composition when administered to mammal with or without bone disease strengthens and helps in bone mineralization process. The composition can be used as a preventive dose for bone demineralization in human.

11 Claims, 4 Drawing Sheets

MICRONUTRIENT AND PLANT EXTRACT COMPOSITION AND METHOD OF IMPROVING BONE HEALTH

FIELD OF TECHNOLOGY

This application describes a micronutrient and plant extract combination and method of using the same for improving bone health.

BACKGROUND

Bone health is very important at every stage in life. Bone mineralization, repair and maintenance is a continuous process and requires good nutrition and exercise to keep it healthy. The body's skeleton forms and grows to its adult size in a process called modeling. It then completely regenerates—or remodels—itself about every 10 years. Remodeling removes old pieces of bone and replaces them with new, fresh bone tissue. This keeps the bone and its cells healthy and strong and allows the bones to supply calcium and other minerals to the body.

Keeping the skeleton in good health requires a balance between removal and replacement of bone tissue. In young, healthy adults, the amount of bone removed and replaced is about the same. This is called balanced bone remodeling. As we age, the remodeling process can shift out of balance, resulting in loss of bone structure and strength, and lead to bone diseases, including osteoporosis.

Maintaining healthy bones requires a continuous supply of nutrients, many of which are not produced in a human body or are available in limited amounts. These include vitamin C for forming proper collagen, the bone skeleton, which is subsequently hardened by the deposition of minerals. Also, bone building minerals such as calcium other minerals and trace elements have to originate from dietary sources. Dietary supplementation with one or a few micronutrients does not assure optimum bone metabolism as each component has a different mechanism of action and interaction with other cellular compounds and can lead to metabolic imbalance. This is why there is a need for a select and experimentally tested composition of essential nutrients that can be applied as a safe and effective measure, such as in a form of a supplement to prevent excessive bone loss and support healthy bone regeneration uniformly through the years.

SUMMARY

In the instant disclosure various combination of micronutrient and plant extract as a composition were used to treat, prevent, support, improve and enhance bone health. In one embodiment a physiological dose for a mammal was calculated based on daily consumption. The micronutrient and plant extract composition was packaged in drug formulation for easy consumption by mammals. The physiological calculations were based on in-vitro experiments and mode of delivery for consumption by human.

In one embodiment, the micronutrient and plant extract composition comprises of a vitamin C, vitamin A (β-carotene), vitamin E, vitamin D3, vitamin K2, folic acid, calcium, magnesium, boron, horsetail extract, zinc, potassium, copper, methylsulfonylmethane (MSM) and stinging nettle extract.

In another embodiment, the concentration of each ingredient in the micronutrient and plant extract composition are vitamin C in the range of 10 mg-20,000 mg, vitamin A (β-carotene) in range of 5 mg-400 mg, vitamin E in range of 10 mg-3,000 mg, vitamin D3 in range of 10 IU-20,000 IU, vitamin K2 in range of 20 mcg-45,000 mcg, folic acid in range of 10 mcg-2,000 mcg, calcium in range of 10 mg-5,000 mg, magnesium in range of 10 mg-5,000 mg, boron in range of 1 mg-70 mg, horsetail extract in range of 10 mg-2,000 mg, zinc in range of 1 mg-1,000 mg, potassium in range of 10 mg-3,500 mg, copper in range of 0.1 mg-50 mg, methylsulfonylmethane in range of 10 mg-8,000 mg and stinging nettle extract in range of 10 mg-5,000 mg.

In one embodiment, a method of increasing bone mineralization by increasing alkaline phosphatase enzyme activity, core-binding factor alpha (1) transcription factor in mineralization of human osteoblasts and reducing sclerostin enzyme activity by administering the micronutrient and plant extract composition.

In one embodiment, a method of increasing bone mineralization by increasing the alkaline phosphate activity in human osteoblast cells using the micronutrient and plant extract composition containing a combination of vitamin C in the range of 10 mg-20,000 mg, vitamin A (β-carotene) in range of 5 mg-400 mg, vitamin E in range of 10 mg-3,000 mg, vitamin D3 in range of 10 IU-20,000 IU, vitamin K2 in range of 20 mcg-45,000 mcg, folic acid in range of 10 mcg-2,000 mcg, calcium in range of 10 mg-5,000 mg, magnesium in range of 10 mg-5,000 mg, boron in range of 1 mg-70 mg, horsetail extract in range of 10 mg-2,000 mg, zinc in range of 1 mg-1,000 mg, potassium in range of 10 mg-3,500 mg, copper in range of 0.1 mg-50 mg, methylsulfonylmethane in range of 10 mg-8,000 mg and stinging nettle extract in range of 10 mg-5,000 mg is disclosed.

In one embodiment, a method of increasing bone mineralization by increasing the alkaline phosphate activity in human osteoblast cells using the micronutrient and plant extract composition containing a combination of vitamin C in the range of 10 mg-20,000 mg, vitamin A (β-carotene) in range of 5 mg-400 mg, vitamin E in range of 10 mg-3,000 mg, vitamin D3 in range of 10 IU-20,000 IU, vitamin K2 in range of 20 mcg-45,000 mcg, folic acid in range of 10 mcg-2,000 mcg, calcium in range of 10 mg-5,000 mg, magnesium in range of 10 mg-5,000 mg, boron in range of 1 mg-70 mg, horsetail extract in range of 10 mg-2,000 mg, zinc in range of 1 mg-1,000 mg, potassium in range of 10 mg-3,500 mg, copper in range of 0.1 mg-50 mg, methylsulfonylmethane in range of 10 mg-8,000 mg and stinging nettle extract in range of 10 mg-5,000 mg.

In one embodiment, a method of administering the micronutrient and plant extract composition as a drug formulation suitable for increasing bone mineralization in mammal containing a combination of vitamin C in the range of 10 mg-20,000 mg, vitamin A (β-carotene) in range of 5 mg-400 mg, vitamin E in range of 10 mg-3,000 mg, vitamin D3 in range of 10 IU-20,000 IU, vitamin K2 in range of 20 mcg-45,000 mcg, folic acid in range of 10 mcg-2,000 mcg, calcium in range of 10 mg-5,000 mg, magnesium in range of 10 mg-5,000 mg, boron in range of 1 mg-70 mg, horsetail extract in range of 10 mg-2,000 mg, zinc in range of 1 mg-1,000 mg, potassium in range of 10 mg-3,500 mg, copper in range of 0.1 mg-50 mg, methylsulfonylmethane in range of 10 mg-8,000 mg and stinging nettle extract in range of 10 mg-5,000 mg are disclosed.

BRIEF DESCRIPTION OF DRAWINGS

Example embodiments are illustrated by way of example and not limitation in the figures of the accompanying drawings, in which like references indicate similar elements and in which.

Others features of the present embodiments will be apparent from the accompanying drawings and from the detailed description that follows.

DETAILED DESCRIPTION

In the instant disclosure the micronutrient and plant extract composition comprises of a vitamin C, vitamin A (β-carotene), vitamin E, vitamin D3, vitamin K2, folic acid, calcium, magnesium, boron, horsetail extract, zinc, potassium, copper, methylsulfonylmethane (MSM) and stinging nettle extract. It may also be disclosed as the micronutrient and plant extract composition consists of a vitamin C, vitamin A (β-carotene), vitamin E, vitamin D3, vitamin K2, folic acid, calcium, magnesium, boron, horsetail extract, zinc, potassium, copper, methylsulfonylmethane (MSM) and stinging nettle extract. The range of physiological dose of the composition depends on mode of delivery. For example oral delivery concentration is different from injection based delivery. Hence the vitamin C in the range of 10 mg-20,000 mg, vitamin A (β-carotene) in range of 5 mg-400 mg, vitamin E in range of 10 mg-3,000 mg, vitamin D3 in range of 10 IU-20,000 IU, vitamin K2 in range of 20 mcg-45,000 mcg, folic acid in range of 10 mcg-2,000 mcg, calcium in range of 10 mg-5,000 mg, magnesium in range of 10 mg-5,000 mg, boron in range of 1 mg-70 mg, horsetail extract in range of 10 mg-2,000 mg, zinc in range of 1 mg-1,000 mg, potassium in range of 10 mg-3,500 mg, copper in range of 0.1 mg-50 mg, methylsulfonylmethane in range of 10 mg-8,000 mg and stinging nettle extract in range of 10 mg-5,000 mg was calculated as a dosage for mammal. The disclosed micronutrient and plant extract composition are used to treat human that are in need of bone remineralization and improve bone density and bone strength. The instant composition works at three different levels that are described below.

Bone ALP is a major regulator of bone mineralization. It hydrolyzes inorganic pyrophosphate, which is a naturally occurring inhibitor of mineralization. Bone ALP also provides inorganic phosphate (from pyrophosphate and organic phosphomonoesters) for the synthesis of hydroxyapatite.

Core-binding factor alpha 1 (Cbfa1) is an essential transcription factor for osteoblastic differentiation and osteogenesis. Bone morphogenetic protein (BMP) is also a powerful inducer of differentiation of pluripotent mesenchymal cells to osteoblast lineage and bone formation.

Skeletal mineralization relies on a tightly regulated connection between cell activity and extracellular environment. Researchers in skeletal biology analyze the cellular and molecular events underlying skeletal matrix formation and maintenance, and the mechanisms that promote and limit the mineralization of the matrix. Alizarin (1,2-dihydroxyanthraquinone), which emits a red signal under fluorescent green light, has been used for detecting mineralization of osteocytes in in vitro and in vivo labelling for many decades.

Sclerostin is a small protein expressed by the SOST gene in osteocytes, bone cells that respond to mechanical stress applied to the skeleton and appear to play an important role in the regulation of bone remodeling. When sclerostin binds to its receptors on the cell surface of osteoblasts, a downstream cascade of intracellular signaling is initiated, with the ultimate effect of inhibiting osteoblastic bone formation.

Materials and Methods: The experiments are conducted in-vitro and the micronutrient and plant extract composition are tested individually and in combination in several assays to show the efficacy and preventive nature of the said composition in treating bone demineralization. The following compounds, with the purity between 90%-98% according to the manufacturer, were obtained from Sigma (St. Louis, Mo.): vitamin A, vitamin C, vitamins D3, and folic acid. The compounds such as vitamin E, vitamin K2, zinc, magnesium, calcium, copper, potassium, MSM, and nettle extract, with the purity between 90%-98% according to the manufacturer, were purchased from Powder City (York, Pa.). Horsetail extract (silica), with the purity between 97%-99% according to the manufacturer, were from Monterey Bay Spice (Watsonville, Calif.). Boron was from Pure Encapsulations (Sudbury, Mass.). Cells and cell lines were from ATCC (Manassas, Va.) or Lonza (Walkersville, Md.).

The following assays were performed according to manufactures' protocols. In vitro differentiation (alkaline phosphatase activity (ALP) and core-binding factor alpha 1 (Cbfa-1) as a marker) assay: Human osteoblasts ($1 \times 10^5$ cells/well of a 96-well plate) in a 100 μl cell culture medium were exposed to select micronutrients and plant extracts (0.1-5 μg/ml) for 48 h at 37° C., and lysed with assay buffer. Subsequently, 5 mM p-nitrophenyl phosphate (pNPP), as a phosphate substrate for alkaline phosphates, was added into all experimental wells for 1 h, followed by a stop solution. The absorbance was measured at 450 nm within 5 min. using a microplate reader.

Cbfa-1 assay: Human osteoblasts were plated into 96-well plates at a density of $1 \times 10^6$ cells/ml per well in a 200 μl volume, and exposed to select micronutrients and plant extracts (0.1-5 μg/ml) for 5 days at 37° C. Afterwards, each well wash washed 3 times with PBS and fixed/permeabilized with 4% paraformaldehyde/0.1% Triton-X 100 for 1 h at 4° C. In the next step, the cells were washed 3 times with PBS and blocked with 1% BSA followed by incubation with primary antibody against core-binding factor alpha 1 for 2 h at room temperature. Than cells were washed again 3 times with PBS and incubated with HRP-conjugated secondary antibody against core-binding factor alpha 1 for 2 h at room temperature. Finally, cells were washed 3 times with PBS and TMB peroxidase substrate was added followed by a stop solution and the absorbance was measured at 450 nm within 5 min. using a microplate reader.

In vitro mineralization assay: Human osteoblasts were plated into 96-well plates at a density of $1 \times 10^6$ cells/ml per well in a 150 μl volume, and exposed every fourth day to fresh additions of select micronutrients and plant extracts (5-20 μg/ml) for a total period of 3 weeks at 37° C. Afterwards, each well wash washed 3 times with PBS and alizarin red S (100 μl) was added to each well for 45 min followed again by three washes with distilled water. Next 100 μl of PBS was added to all wells and the absorbance was measured at 405 nm within 5 min. using a microplate reader.

In vitro bone matrix resorption (sclerostin as a marker) assay: Human osteoblasts were plated into 96-well plates at a density of $1 \times 10^6$ cells/ml per well in a 200 μl volume, and exposed to select micronutrients and plant extracts (0.1-5 μg/ml) for 2 weeks at 37° C. Subsequently, each well was washed 3 times with PBS and fixed/permeabilized with 4% paraformaldehyde/0.1% Triton-X 100 for 1 h at 4° C. Next cells were washed 3 times with PBS and blocked with 1% BSA followed by incubation with primary antibody against sclerostin for 2 h at room temperature. The cells were washed again 3 times with PBS and incubated with HRP-conjugated secondary antibody against core-binding factor alpha 1 for 2 h at room temperature. Finally, cells were washed 3 times with PBS and TMB peroxidase substrate was added followed by a stop solution and the absorbance was measured at 450 nm within 5 min. using a microplate reader.

Statistical Analysis:

Means and standard deviations were determined for all experiments and Student's t test analysis was applied to determine statistically significant differences. Statistical analysis was performed by two-sample paired t-test using GraphPad statistical software.

Figure 1:
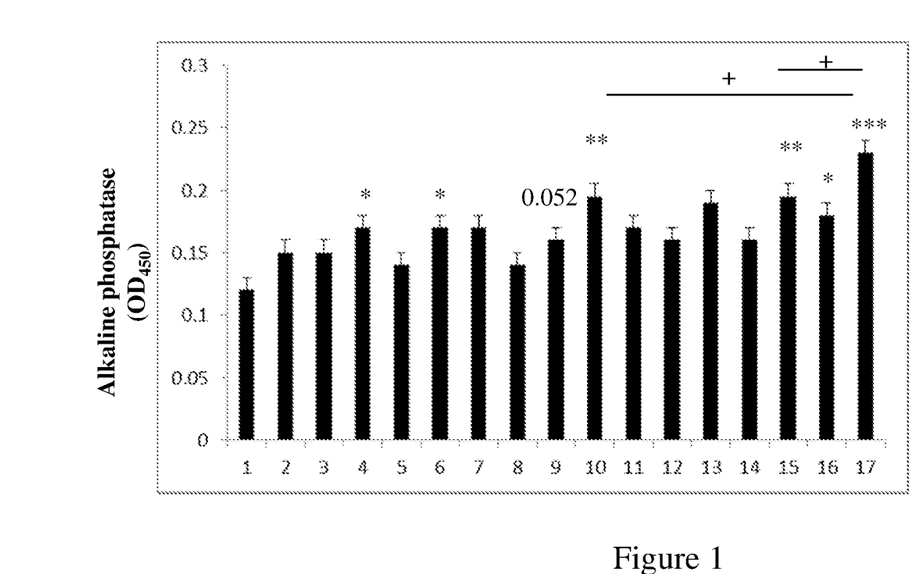
FIG. 1 shows Alkaline phosphatase (ALP) activity in human osteoblasts after exposure to select micronutrients and plant extracts.

FIG. 1 shows alkaline phosphatase (ALP) activity level in human osteoblasts after exposure to select micronutrients and plant extracts (0.1-5 µg/ml) for 48 h at 37° C. and expressed as the mean±standard deviation (n=4). Value significantly different from corresponding control at * $p<0.05$,  $p<0.01$, * $p<0.001$, +$p<0.05$ compared to the most stimulating agents (boron and MSM), respectively. Statistically significant increase of alkaline phosphatase activity in human osteoblasts treated with the composition of 15 (comprising vitamins, minerals and plant extracts) was observed when compared to the control (line 1) and to the most stimulating agents (i.e., boron line 10 and MSM line 15 respectively). The bar numbers in FIG. 1 is described as follows: 1—control; 2—vitamin C; 3—vitamin A (beta carotene); 4—vitamin E; 5—vitamin D3; 6—vitamin k2; 7—folic acid; 8—calcium; 9—magnesium; 10—boron; 11—horsetail extract; 12—zinc; 13—potassium; 14—copper; 15—MSM; 16—stinging nettle extract, 17—Mix of ingredients 15 ingredients (2-16).

Figure 2:
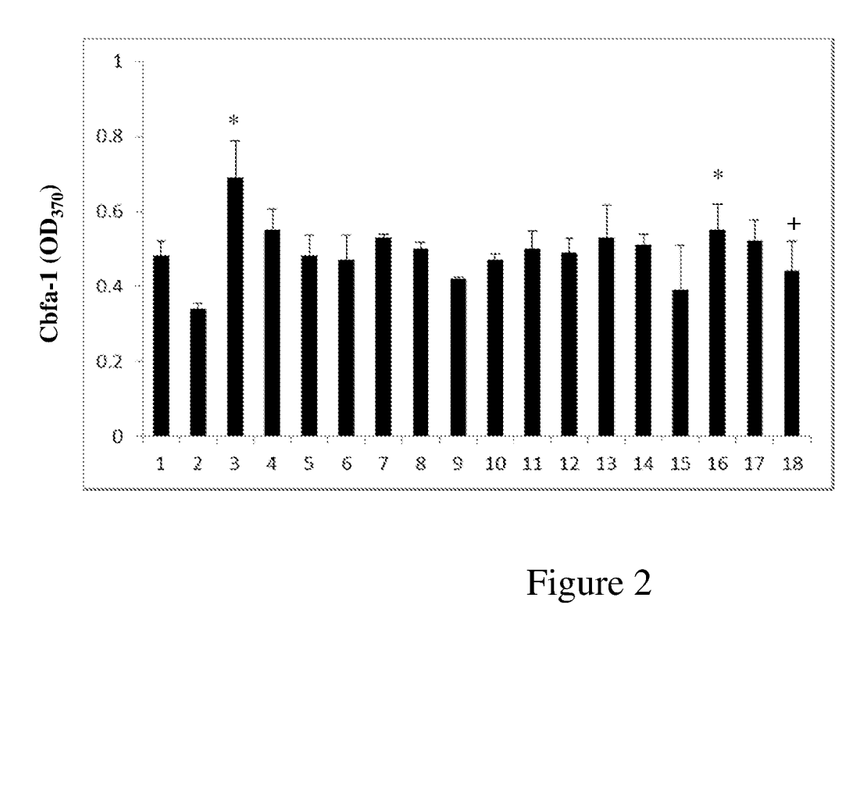
FIG. 2 shows core-binding factor alpha 1 (Cbfa-1) detection in human osteoblasts after treatment with different micronutrients and plant extracts.

FIG. 2 shows the effects of select micronutrients and plant extracts (0.1-5 µg/ml) on core-binding factor alpha 1 (Cbfa-1) detection in human osteoblasts after treatment for 5 days at 37° C. The results are expressed as the mean±standard deviation (n=4). Due to different final concentrations of DMSO in individual samples and the mix, two controls were applied: 0.05-0.1% DMSO and 0.6% DMSO. Value significantly different from control with 0.05-0.1% DMSO (*) $p<0.05$, from control with 0.6% DMSO (+) $p<0.05$. Statistically significant increase in core-binding factor alpha 1 level in human osteoblasts treated with the composition of vitamin C, vitamin A (β-carotene), vitamin E, vitamin D3, vitamin K2, folic acid, calcium, magnesium, boron, horsetail extract, zinc, potassium, copper, methylsulfonylmethane (MSM) and stinging nettle extract was observed when compared to the corresponding control (0.6% DMSO). The figure shows numbered bars and they represent: 1. control with 0.05-0.1% DMSO, 2: Control with 0.6% DMSO, 3: vitamin C, 4: vitamin A (b-Carotene), 5: vitamin E, 6: vitamin D3, 7: vitamin K2, 8: folic Acid, 9: calcium, 10: magnesium, 11: boron, 12: horsetail extract, 13: zinc, 14: potassium, 15: copper, 16: MSM, 17: stinging nettle extract and 18: micronutrient and plant extract composition.

Figure 3:
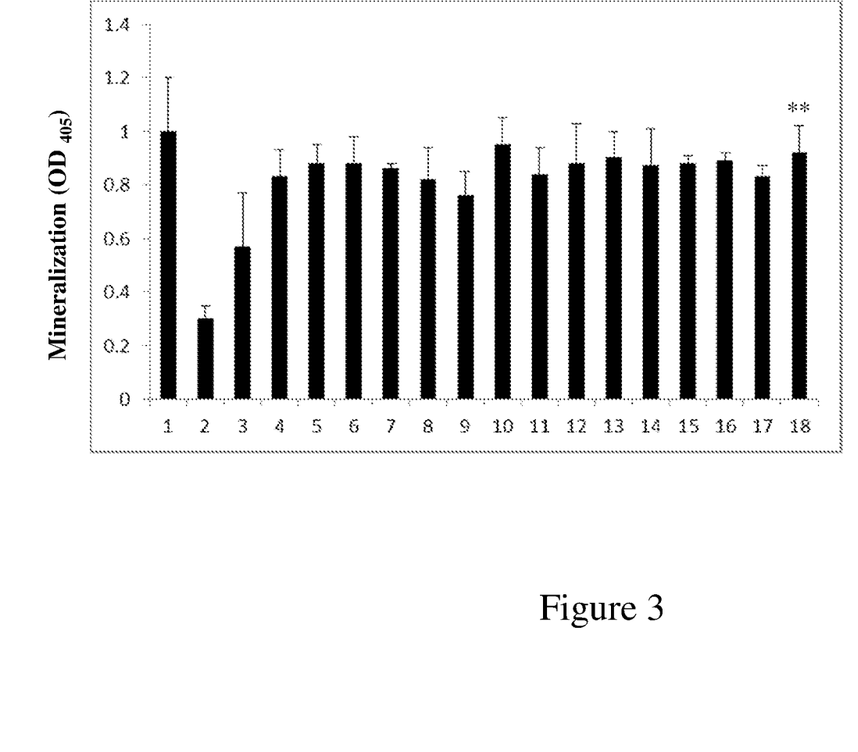
FIG. 3 shows mineralization level of human osteoblasts stimulated by different micronutrients and plant extracts.

FIG. 3 shows changes in the mineralization level of human osteoblasts in the presence of select micronutrients and plant extracts (0.1-5 µg/ml) after exposure for 3 weeks at 37° C. Mineralization was assessed by the alizarin red S staining method and expressed as the mean±standard deviation (n=4). Value significantly different from corresponding control (i.e., with 0.7% DMSO) at ** $p<0.01$. Statistically significant increase in mineralization of human osteoblasts was observed with the combination of vitamin C, vitamin A (β-carotene), vitamin E, vitamin D3, vitamin K2, folic acid, calcium, magnesium, boron, horsetail extract, zinc, potassium, copper, methylsulfonylmethane (MSM) and stinging nettle extract when compared to the corresponding control (0.7% DMSO). FIG. 3 shows numbered bars that represent: 1: Control with 0.05-0.1% DMSO, 2: Control with 0.7% DMSO, 3: vitamin C, 4: vitamin A (b-carotene), 5: vitamin E, 6: vitamin D3, 7: vitamin K2, 8: folic Acid, 9: calcium, 10: magnesium, 11: boron, 12: horsetail extract, 13: zinc, 14: potassium, 15: copper, 16: methylsulfonylmethane, 17: stinging nettle extract, 18: Micronutrient and plant extract composition.

Figure 4:
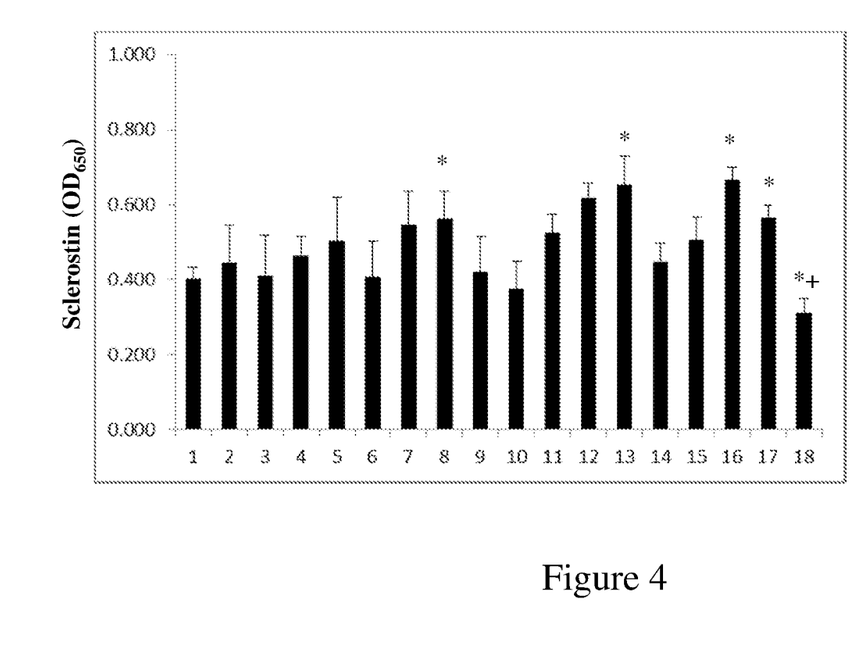
FIG. 4 shows Sclerostin detection in human osteoblasts after treatment with different micronutrients and plant extracts.

FIG. 4 shows changes in Sclerostin levels in human osteoblasts after their treatment with select micronutrients and plant extracts (0.1-5 µg/ml) for 2 weeks at 37° C. The results are expressed as the mean±standard deviation (n=3). Value significantly different from control with 0.05-0.1% DMSO (*) $p<0.05$-$0.01$, from control with 0.6% DMSO (+) $p<0.05$. Statistically significant decrease in sclerostin level in human osteoblasts treated with the composition of vitamin C, vitamin A (β-carotene), vitamin E, vitamin D3, vitamin K2, folic acid, calcium, magnesium, boron, horsetail extract, zinc, potassium, copper, methylsulfonylmethane (MSM) and stinging nettle extract was observed when compared to the corresponding control (with 0.6% DMSO). FIG. 4 shows results of different ingredients as bars and each bar represents-1: Control with 0.05-0.1% DMSO, 2: Control with 0.6% DMSO, 3: vitamin C, 4: vitamin A (b-Carotene), 5: vitamin E, 6: vitamin D3, 7: vitamin K2, 8: folic Acid, 9: calcium, 10: magnesium, 11: boron, 12: horsetail extract, 13: zinc, 14: potassium, 15: copper, 16: methylsulfonylmethane, 17: stinging nettle extract and 18: micronutrient and plant extract composition.

Drug formulations suitable for these administration routes can be produced by adding one or more pharmacologically acceptable carrier to the agent and then treating the micronutrient composition through a routine process known to those skilled in the art to the composition of vitamin C, vitamin A (β-carotene), vitamin E, vitamin D3, vitamin K2, folic acid, calcium, magnesium, boron, horsetail extract, zinc, potassium, copper, methylsulfonylmethane (MSM) and stinging nettle extract. The mode of administration includes, but is not limited to, non-invasive peroral, topical (for example, transdermal), enteral, transmucosal, targeted delivery, sustained-release delivery, delayed release, pulsed release and parenteral methods. Peroral administration may be administered both in liquid and dry state. In one embodiment, pharmaceutical micronutrient composition would be more specifically micronutrient and plant extract composition.

Formulations suitable for oral administration may be in the form of capsules, cachets, pills, tablets, lozenges (using a flavored bases, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin or sucrose and acacia), each containing a predetermined amount of the disclosed composition as an active ingredient. Subject compositions may also be administered as a bolus, electuary or paste.

When an oral solid drug product is prepared, pharmaceutical micronutrient composition is mixed with an excipient (and, if necessary, one or more additives such as a binder, a disintegrant, a lubricant, a coloring agent, a sweetening agent, and a flavoring agent), and the resultant mixture is processed through a routine method, to thereby produce an oral solid drug product such as tablets, coated tablets, granules, powder or capsules. Additives may be those generally employed in the art. Examples of excipients include lactate, sucrose, sodium chloride, glucose, starch, calcium carbonate, kaolin, microcrystalline cellulose and silicic acid. Binders include water, ethanol, propanol, simple syrup, glucose solution, starch solution, liquefied gelatin, carboxymethylcellulose, hydroxypropyl cellulose, hydroxypropyl starch, methyl cellulose, ethyl cellulose, shellac, calcium phosphate and polyvinyl pyrrolidone. Disintegrants include dried starch, sodium arginate, powdered agar, sodium hydroxy carbonate, calcium carbonate, sodium lauryl sulfate, monoglyceryl stearate and lactose. Lubricants include purified talc, stearic acid salts, borax and polyethylene glycol. Sweetening agents include sucrose, orange peel, citric acid and tartaric acid.

When a liquid drug product for oral administration is prepared, pharmaceutical micronutrient composition is mixed with an additive such as a sweetening agent, a buffer, a stabilizer, or a flavoring agent, and the resultant mixture is processed through a routine method, to produce an orally administered liquid drug product such as an internal solution medicine, syrup or elixir. Examples of the sweetening agent include vanillin; examples of the buffer include sodium citrate; and examples of the stabilizer include tragacanth, acacia, and gelatin.

For the purposes of transdermal (e.g., topical) administration, dilute sterile, aqueous or partially aqueous solutions (usually in about 0.1% to 5% concentration), otherwise similar to the above parenteral solutions, may be prepared with pharmaceutical micronutrient composition.

Formulations containing pharmaceutical micronutrient composition for rectal or vaginal administration may be presented as a suppository, which may be prepared by mixing a subject composition with one or more suitable non-irritating carriers, comprising, for example, cocoa butter, polyethylene glycol, a suppository wax or a salicylate, which is solid at room temperature, but liquid at body temperature and, therefore, will melt in the appropriate body cavity and release the encapsulated compound(s) and composition(s). Formulations that are suitable for vaginal administration also include pessaries, tampons, creams, gels, pastes, foams or spray formulations containing such carriers as are known in the art to be appropriate.

A targeted-release portion for capsules containing pharmaceutical micronutrient composition can be added to the extended-release system by means of either applying an immediate-release layer on top of the extended release core; using coating or compression processes, or in a multiple-unit system such as a capsule containing extended- and immediate-release beads.

When used with respect to a pharmaceutical micronutrient composition, the term "sustained release" is art recognized. For example, a therapeutic composition that releases a substance over time may exhibit sustained-release characteristics, in contrast to a bolus type administration in which the entire amount of the substance is made biologically available at one time. In particular embodiments, upon contact with body fluids, including blood, spinal fluid, mucus secretions, lymph or the like, one or more of the pharmaceutically acceptable excipients may undergo gradual or delayed degradation (e.g., through hydrolysis), with concomitant release of any material incorporated therein, e.g., a therapeutic and/or biologically active salt and/or composition, for a sustained or extended period (as compared with the release from a bolus). This release may result in prolonged delivery of therapeutically effective amounts of any of the therapeutic agents disclosed herein.

Current efforts in the area of drug delivery include the development of targeted delivery, in which the drug is only active in the target area of the body (for example, mucous membranes such as in the nasal cavity), and sustained-release formulations, in which the pharmaceutical micronutrient composition is released over a period of time in a controlled manner from a formulation. Types of sustained release formulations include liposomes, drug-loaded biodegradable microspheres and pharmaceutical micronutrient composition polymer conjugates.

Delayed-release dosage formulations are created by coating a solid dosage form with a film of a polymer, which is insoluble in the acid environment of the stomach, but soluble in the neutral environment of the small intestine. The delayed-release dosage units can be prepared, for example, by coating a pharmaceutical micronutrient composition with a selected coating material. The pharmaceutical micronutrient composition may be a tablet for incorporation into a capsule, a tablet for use as an inner core in a "coated core" dosage form, or a plurality of drug-containing beads, particles or granules, for incorporation into either a tablet or a capsule. Preferred coating materials include bioerodible, gradually hydrolysable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract, or slowly erode as the dosage form passes through the gastrointestinal tract, while enzymatically degradable polymers are degraded by bacterial enzymes present in the lower gastrointestinal tract, particularly in the colon. Alternatively, a delayed-release tablet may be formulated by dispersing a drug within a matrix of a suitable material such as a hydrophilic polymer or a fatty compound. Suitable hydrophilic polymers include, but are not limited to, polymers or copolymers of cellulose, cellulose ester, acrylic acid, methacrylic acid, methyl acrylate, ethyl acrylate and vinyl or enzymatically degradable polymers or copolymers as described above. These hydrophilic polymers are particularly useful for providing a delayed-release matrix. Fatty compounds for use as a matrix material include, but are not limited to, waxes (e.g., carnauba wax) and glycerol tristearate. Once the active ingredient is mixed with the matrix material, the mixture can be compressed into tablets.

A pulsed-release dosage is one that mimics a multiple dosing profile without repeated dosing, and typically allows at least a twofold reduction in dosing frequency as compared with the drug presented as a conventional dosage form (e.g., as a solution or prompt drug-releasing, conventional solid dosage form). A pulsed-release profile is characterized by a time period of no release (lag time) or reduced release, followed by rapid drug release. These can be formulated for critically ill patients using the instant pharmaceutical micronutrient composition.

The phrases "parenteral administration" and "administered parenterally" as used herein refer to modes of administration other than enteral and topical, such as injections, and include without limitation intravenous, intramuscular, intrapleural, intravascular, intrapericardial, intra-arterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The micronutrient composition disclosed herein, suitable for parenteral administration, comprise one or more subject compositions in combination with one or more pharmaceutically acceptable sterile, isotonic, aqueous, or non-aqueous solutions, dispersions, suspensions or emulsions, or sterile powders, which may be reconstituted into sterile injectable solutions or dispersions just prior to use, and which may contain antioxidants, buffers, bacteriostats, solutes that render the formulation isotonic within the blood of the intended recipient, or suspending or thickening agents.

When an injection product is prepared, pharmaceutical micronutrient composition is mixed with an additive such as a pH regulator, a buffer, a stabilizer, an isotonicity agent or a local anesthetic, and the resultant mixture is processed through a routine method, to thereby produce an injection for subcutaneous injection, intramuscular injection, or intravenous injection. Examples of the pH regulator or buffer include sodium citrate, sodium acetate and sodium phosphate; examples of the stabilizer include sodium pyrosulfite, EDTA, thioglycolic acid, and thiolactic acid; examples of the local anesthetic include procaine hydrochloride and lidocaine hydrochloride; and examples of the isotonicity agent include sodium chloride and glucose.

Described herein are ready-to-use, premixed pharmaceutical compositions of vitamin C in the range of 10 mg-20,000 mg, vitamin A (β-carotene) in range of 5 mg-400 mg, vitamin E in range of 10 mg-3,000 mg, vitamin D3 in range of 10 IU-20,000 IU, vitamin K2 in range of 20 mcg-45,000 mcg, folic acid in range of 10 mcg-2,000 mcg, calcium in range of 10 mg-5,000 mg, magnesium in range of 10 mg-5,000 mg, boron in range of 1 mg-70 mg, horsetail extract in range of 10 mg-2,000 mg, zinc in range of 1 mg-1,000 mg, potassium in range of 10 mg-3,500 mg, copper in range of 0.1 mg-50 mg, methylsulfonylmethane in range of 10 mg-8,000 mg and stinging nettle extract in range of 10 mg-5,000 mg or pharmaceutically acceptable salts thereof, which are suitable for continuous intravenous infusion. By providing ready-to-use, premixed pharmaceutical compositions with a buffered pH, these pharmaceutical compositions are stable at room temperature for at least one year. When stored at room temperature, the pharmaceutical compositions exhibit between 0% to about 15% loss of drug and between 0% to about 3% (w/w) total impurity formation over an eighteen to twenty four month period.

Additional benefits of the pre-mixed, ready-to-use, injectable pharmaceutical compositions include convenience and ease of use as compared to an ampul formulation, improved safety for patients due to elimination of dosage errors and solution contamination, reduction of medical waste, and ease of administration in emergency situations. The present disclosure relates to premixed pharmaceutical compositions comprising vitamin C in the range of 10 mg-20,000 mg, vitamin A (β-carotene) in range of 5 mg-400 mg, vitamin E in range of 10 mg-3,000 mg, vitamin D3 in range of 10 IU-20,000 IU, vitamin K2 in range of 20 mcg-45,000 mcg, folic acid in range of 10 mcg-2,000 mcg, calcium in range of 10 mg-5,000 mg, magnesium in range of 10 mg-5,000 mg, boron in range of 1 mg-70 mg, horsetail extract in range of 10 mg-2,000 mg, zinc in range of 1 mg-1,000 mg, potassium in range of 10 mg-3,500 mg, copper in range of 0.1 mg-50 mg, methylsulfonylmethane in range of 10 mg-8,000 mg and stinging nettle extract in range of 10 mg-5,000 mg or pharmaceutically acceptable salts thereof, one or more tonicity agents, and a buffer. In some embodiments, the premixed pharmaceutical compositions further comprise one or more tonicity agents.

Typically, tonicity agents are used to adjust the osmolality of the premixed pharmaceutical compositions to bring it closer to the osmotic pressure of body fluids, such as blood or plasma. In some embodiments the tonicity of the premixed formulation can be modified by adjusting the concentration of buffer and/or other components present in the premixed formulation. Adjuvants are used to enhance the immune response. Various types of adjuvants are available. Haptens and Freund's adjuvant may also be used to produce water-in-oil emulsions of immunogens.

The phrase "pharmaceutically acceptable" is art recognized. In certain embodiments, the term includes compositions, polymers and other materials and/or dosage forms that are within the scope of sound medical judgment, suitable for use in contact with the tissues of mammals, both human beings and animals, without excessive toxicity, irritation, allergic response or other problem or complication, commensurate with a reasonable benefit-risk ratio.

The phrase "pharmaceutically acceptable carrier" is art recognized, and includes, for example, pharmaceutically acceptable materials, compositions or vehicles, such as a liquid or solid filler, diluent, solvent or encapsulating material involved in carrying or transporting any subject composition from one organ or portion of the body, to another organ or portion of the body. Each carrier must be "acceptable" in the sense of being compatible with the other ingredients of a subject composition, and not injurious to the patient. In certain embodiments, a pharmaceutically acceptable carrier is non-pyrogenic. Some examples of materials that may serve as pharmaceutically acceptable carriers include: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the pharmaceutical micronutrient compositions described herein are formulated in a manner such that said compositions will be delivered to a mammal in a therapeutically effective amount, as part of a prophylactic, preventive or therapeutic treatment to overcome the infection caused by corona viruses (irrespective of the type).

In certain embodiments, the dosage of the pharmaceutical micronutrient compositions, which may be referred to as therapeutic composition provided herein, may be determined by reference to the plasma concentrations of the therapeutic composition or other encapsulated materials. For example, the blood samples may be tested for their immune response to their corresponding viral load or lack thereof.

The therapeutic pharmaceutical micronutrient composition provided by this application may be administered to a subject in need of treatment by a variety of conventional routes of administration, including orally, topically, parenterally, e.g., intravenously, subcutaneously or intramedullary. Further, the therapeutic compositions may be administered intranasally, as a rectal suppository, or using a "flash" formulation, i.e., allowing the medication to dissolve in the mouth without the need to use water. Furthermore, the compositions may be administered to a subject in need of treatment by controlled-release dosage forms, site-specific drug delivery, transdermal drug delivery, patch-mediated drug delivery (active/passive), by stereotactic injection, or in nanoparticles.

Expressed in terms of concentration, an active ingredient can be present in the therapeutic compositions of the present invention for localized use via the cutis, intranasally, pharyngolaryngeally, bronchially, intravaginally, rectally or ocularly.

For use as aerosols, the active ingredients can be packaged in a pressurized aerosol container together with a gaseous or liquefied propellant, for example dichlorodifluoromethane, carbon dioxide, nitrogen, propane and the like, with the usual adjuvants such as cosolvents and wetting agents, as may be necessary or desirable. The most common routes of administration also include the preferred transmucosal (nasal, buccal/sublingual, vaginal, ocular and rectal) and inhalation routes.

In addition, in certain embodiments, the subject pharmaceutical micronutrient composition of the present application may be lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration a combination thereof. The formulations may conveniently be presented in unit dosage form and may be prepared by any methods well known in the art of pharmacy. The amount of a subject pharmaceutical micronutrient composition that may be combined with a carrier material to produce a single dose may vary depending upon the subject being treated and the particular mode of administration.

The therapeutically acceptable amount described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may, for example, contain 0.005-90% w/w, for instance 0.005-50%, 0.005-5% w/w, or 0.01-1.0% w/w, of medicament relative to the total weight of the formulation.

Examples of suitable aqueous and non-aqueous carriers that may be employed in the pharmaceutical micronutrient composition include water, ethanol, polyols (such as glycerol, propylene glycol, polyethylene glycol and the like), and suitable mixtures thereof, vegetable oils such as olive oil, and injectable organic esters such as ethyl oleate. Proper fluidity may be maintained, for example by the use of coating materials such as lecithin, by the maintenance of the required particle size in the case of dispersions, and by the use of surfactants.

What is claimed is:

1. A micronutrient and plant extract composition consisting of:
    vitamin C, vitamin A, vitamin E, vitamin D3, vitamin K2, folic acid, calcium, magnesium, boron, horsetail extract, zinc, potassium, copper, methylsulfonylmethane, stinging nettle extract, and optionally one or a combination of a pharmaceutically acceptable carrier, excipient, liquified propellant, buffer, pH regulator, stabilizer, coating, or flavoring agent, wherein the composition is formulated as a tablet, coated tablet, capsule, pill, intranasal formulation, lozenge, emulsion, pastille, suppository, paste, aerosol, or injectable solution.

2. The micronutrient and plant extract composition of claim 1, wherein vitamin C is in the range of 10 mg-20,000 mg, vitamin A is in the range of 5 mg-400 mg, vitamin E is in the range of 10 mg-3,000 mg, vitamin D3 is in the range of 10 IU-20,000 IU, vitamin K2 is in the range of 20 mcg-45,000 mcg, folic acid is in the range of 10 mcg-2,000 mcg, calcium is in the range of 10 mg-5,000 mg, magnesium is in the range of 10 mg-5,000 mg, boron is in the range of 1 mg-70 mg, horsetail extract is in the range of 10 mg-2,000 mg, zinc is in the range of 1 mg-1,000 mg, potassium is in the range of 10 mg-3,500 mg, copper is in the range of 0.1 mg-50 mg, methylsulfonylmethane is in the range of 10 mg-8,000 mg and stinging nettle extract is in the range of 10 mg-5,000 mg.

3. The micronutrient and plant extract composition of claim 2, wherein the micronutrient and plant extract composition is formulated for treating a mammal to improve bone mineralization.

4. The micronutrient and plant extract composition of claim 3, wherein the mammal is human.

5. A method of improving bone mineralization in a mammal comprising:
    administering to the mammal in need thereof a micronutrient and plant extract composition, wherein the micronutrient and plant extract composition is vitamin C, vitamin A, vitamin E, vitamin D3, vitamin K2, folic acid, calcium, magnesium, boron, horsetail extract, zinc, potassium, copper, methylsulfonylmethane and stinging nettle extract combined at a specific range, wherein the specific range is vitamin C in the range of 10 mg-20,000 mg, vitamin A in the range of 5 mg-400 mg, vitamin E in the range of 10 mg-3,000 mg, vitamin D3 in the range of 10 IU-20,000 IU, vitamin K2 in the range of 20 mcg-45,000 mcg, folic acid in the range of 10 mcg-2,000 mcg, calcium in the range of 10 mg-5,000 mg, magnesium in the range of 10 mg-5,000 mg, boron in the range of 1 mg-70 mg, horsetail extract in the range of 10 mg-2,000 mg, zinc in the range of 1 mg-1,000 mg, potassium in the range of 10 mg-3,500 mg, copper in the range of 0.1 mg-50 mg, methylsulfonylmethane in the range of 10 mg-8,000 mg and stinging nettle extract in the range of 10 mg-5,000 mg, wherein the composition is formulated as a tablet, coated tablet, capsule, pill, intranasal formulation, lozenge, emulsion, pastille, suppository, paste, aerosol, or injectable solution.

6. The method of claim 5, further comprising;
    decreasing a sclerostin level in a human osteoblasts treated with the said composition to improve bone health.

7. The method of claim 5, further comprising;
    increasing a core-binding factor alpha 1 level in human osteoblasts treated with the said composition to improve bone mineralization.

8. The method of claim 5, further comprising;
    increasing a level of alkaline phosphatase activity in human osteoblasts by treating with the said composition to improve bone mineralization.

9. A method of increasing a bone mineralization comprising;
    treating a mammal with a need for improving bone health by administering a micronutrient and plant extract composition to the mammal, wherein the micronutrient and plant extract composition consists of vitamin C, vitamin A, vitamin E, vitamin D3, vitamin K2, folic acid, calcium, magnesium, boron, horsetail extract, zinc, potassium, copper, methylsulfonylmethane and stinging nettle extract combined at a specific range, wherein the composition consists of vitamin C in the range of 10 mg-20,000 mg, vitamin A in the range of 5 mg-400 mg, vitamin E in the range of 10 mg-3,000 mg, vitamin D3 in the range of 10 IU-20,000 IU, vitamin K2 in the range of 20 mcg-45,000 mcg, folic acid in the range of 10 mcg-2,000 mcg, calcium in the range of 10 mg-5,000 mg, magnesium in the range of 10 mg-5,000 mg, boron in the range of 1 mg-70 mg, horsetail extract in the range of 10 mg-2,000 mg, zinc in the range of 1 mg-1,000 mg, potassium in the range of 10 mg-3,500 mg, copper in the range of 0.1 mg-50 mg, methylsulfonylmethane in the range of 10 mg-8,000 mg and stinging nettle extract in the range of 10 mg-5,000 mg, wherein the composition is formulated as a tablet, coated tablet, capsule, pill, intranasal formulation, lozenge, emulsion, pastille, suppository, paste, aerosol, or injectable solution.

10. The method of claim 9, wherein the wherein the mammal is human.

11. The method of claim 9, further comprising;
formulating the micronutrient and plant extract composition for human consumption.

\* \* \* \* \*